US006790215B2

(12) United States Patent
Findlay, III et al.

(10) Patent No.: US 6,790,215 B2
(45) Date of Patent: Sep. 14, 2004

(54) METHOD OF USE FOR PERCUTANEOUS MATERIAL REMOVAL DEVICE AND TIP

(75) Inventors: Thomas R. Findlay, III, Laguna Niguel, CA (US); James R. Madonia, Westminster, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 09/798,234

(22) Filed: Mar. 2, 2001

(65) Prior Publication Data

US 2003/0229369 A1 Dec. 11, 2003

Related U.S. Application Data

(63) Continuation-in-part of application No. 09/308,038, filed on Apr. 30, 1999, now Pat. No. 6,238,405, which is a continuation-in-part of application No. 09/766,150, filed on Jan. 18, 2001.

(30) Foreign Application Priority Data

Nov. 11, 1999  (WO) .............................. PCT/US99/26845

(51) Int. Cl.[7] .............................................. A61B 17/00
(52) U.S. Cl. ...................................................... 606/159
(58) Field of Search ............................... 606/159, 167, 606/171, 172, 174, 180; 604/22

(56) References Cited

U.S. PATENT DOCUMENTS

| | | |
|---|---|---|
| 3,614,953 A | 10/1971 | Moss |
| 3,683,891 A | 8/1972 | Eskridge et al. |
| 3,749,085 A | 7/1973 | Willson et al. |
| 3,937,222 A | 2/1976 | Banko |
| 3,976,077 A | 8/1976 | Kerfoot, Jr. |
| 4,177,797 A | 12/1979 | Baylis et al. |
| 4,649,919 A | 3/1987 | Thimsen et al. |
| 4,653,496 A | 3/1987 | Bundy et al. |
| 4,669,469 A | 6/1987 | Gifford, III et al. |
| 4,679,558 A | 7/1987 | Kensey et al. |
| 4,696,667 A | 9/1987 | Masch |
| 4,844,064 A | 7/1989 | Thimsen et al. |
| 5,064,435 A | 11/1991 | Porter .......................... 623/12 |

(List continued on next page.)

FOREIGN PATENT DOCUMENTS

| | | |
|---|---|---|
| DE | 8900059 | 5/1989 |
| RU | 442795 | 9/1974 |
| RU | 665908 | 6/1979 |
| WO | WO 89/06517 | 7/1989 |
| WO | WO 95/21576 | 8/1995 |
| WO | 96/11648 | 4/1996 |
| WO | WO 98/24372 | 6/1998 |

OTHER PUBLICATIONS

International Search Report for PCT/US99/26845, Filed Nov. 11, 1999.

*Primary Examiner*—Kevin T. Truong
(74) *Attorney, Agent, or Firm*—Rajiv Yadav

(57) ABSTRACT

A method of removing material from a body lumen in a patient in need of such removal, comprising advancing a catheter-mounted device having a distal material removal tip including a hollow housing and a member rotatable therewithin, rotating the rotatable member, drawing the material into the housing, shearing the material in the housing between relatively rotating shearing members to reduce the clogging propensity of the material, and removing the sheared material from within said housing as the material removal tip is advanced through the vessel. In another embodiment, the rotatable member of the invention includes grinding member for grinding the material prior to the contact of the material with the shearing member. An article of manufacture that includes packaging material and instructions in the method of the invention contained within the packaging material is also taught.

24 Claims, 6 Drawing Sheets

U.S. PATENT DOCUMENTS

| | | | |
|---|---|---|---|
| 5,397,345 A | 3/1995 | Lazarus | 623/1 |
| 5,423,799 A | 6/1995 | Shiu | |
| 5,443,497 A | 8/1995 | Venbrux | 623/1 |
| 5,489,295 A | 2/1996 | Piplani et al. | 623/1 |
| 5,522,880 A | 6/1996 | Barone et al. | 623/1 |
| 5,562,726 A | 10/1996 | Chuter | 623/1 |
| 5,562,728 A | 10/1996 | Lazarus et al. | 623/1 |
| 5,575,817 A | 11/1996 | Martin | 623/1 |
| 5,609,605 A | 3/1997 | Marshall et al. | 606/191 |
| 5,676,696 A | 10/1997 | Marcade | 623/1 |
| 5,676,697 A | 10/1997 | McDonald | 623/1 |
| 5,683,449 A | 11/1997 | Marcade | 623/1 |
| 5,683,453 A | 11/1997 | Palmaz | 623/1 |
| 5,797,949 A | 8/1998 | Parodi | 606/194 |
| 5,824,039 A | 10/1998 | Piplani et al. | 623/1 |
| 5,824,055 A | 10/1998 | Spiridigliozzi et al. | 623/1 |
| 5,871,536 A | 2/1999 | Lazarus | 623/1 |
| 5,873,882 A | 2/1999 | Straub et al. | |
| 5,876,414 A | 3/1999 | Straub | |
| 6,001,112 A * | 12/1999 | Taylor | 606/159 |

\* cited by examiner

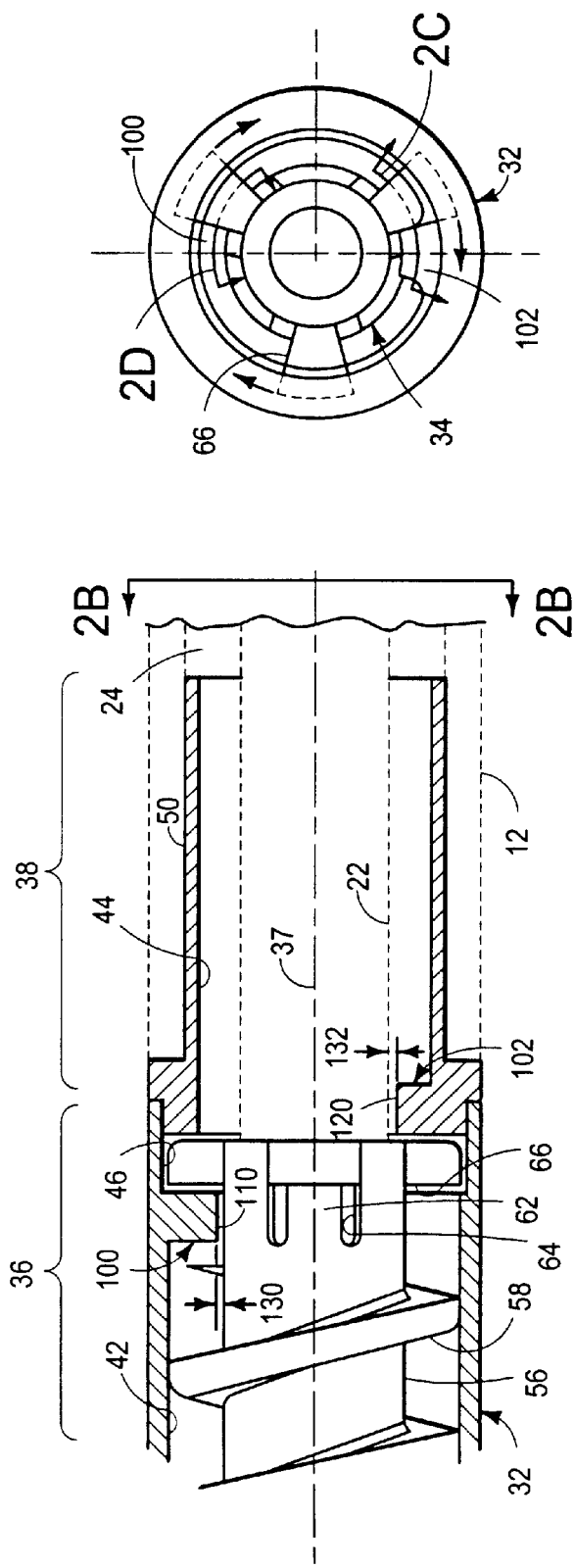
FIG. 2A
FIG. 2B
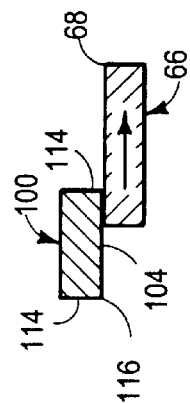
FIG. 2C
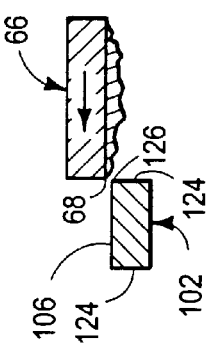
FIG. 2D

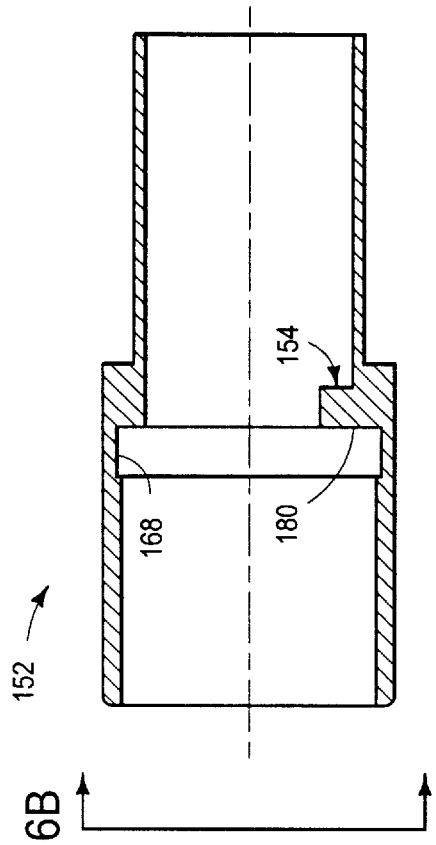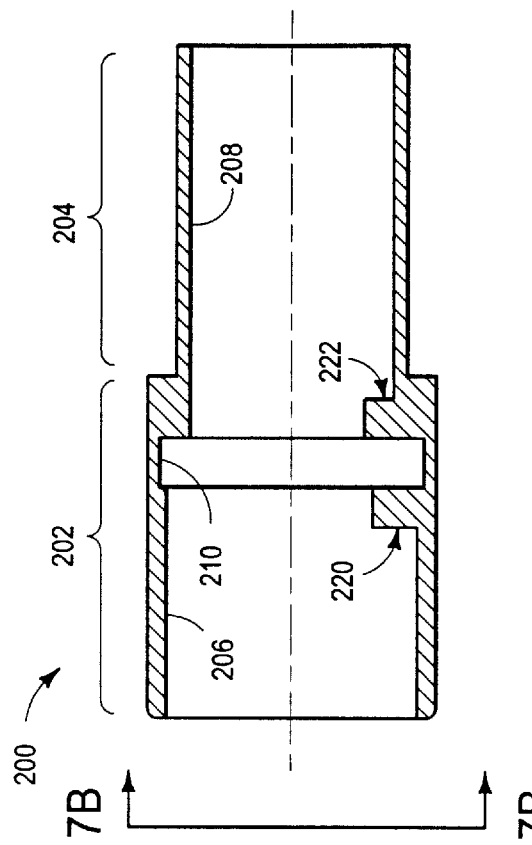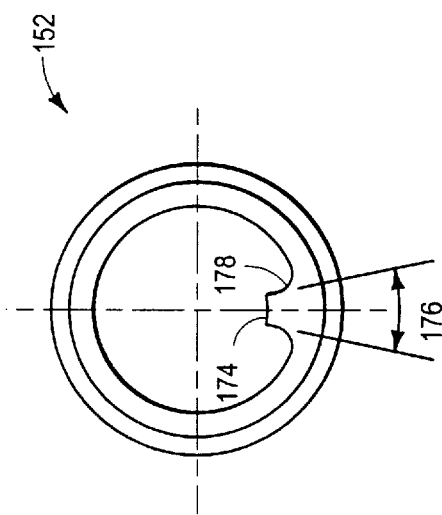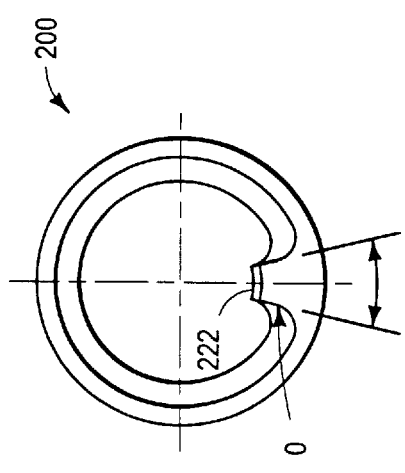

METHOD OF USE FOR PERCUTANEOUS MATERIAL REMOVAL DEVICE AND TIP

CROSS REFERENCE TO RELATED APPLICATIONS

This is a Continuation-in-part, of application Ser. No. 09/308,038, filed Apr. 30, 1999 U.S. Pat. No. 6,238,405, which has been allowed for Issuance as a U.S. Letters Patent, and for which the issue fee has been paid, the entire disclosure of which is hereby expressly incorporated herein by reference. Likewise, co-pending C-I-P, U.S. Ser. No. 09/766,150 filed on Jan. 18, 2001, based upon the same parent, in the name of the same inventors, and assigned to instant assignee is expressly incorporated herein by reference, in its entirety.

BACKGROUND OF THE INVENTION

The present invention is related to methods and apparatus for clearing blocked natural and synthetic vessels, and more specifically, to methods and apparatus for percutaneously clearing material from vessels with a rotating device and suction, without luminal damage.

A variety of techniques and instruments have been developed for use in the removal or repair of obstructive material in vessels and other body passageways. Such material may include atheromas, thrombi, or emboli. An atheroma is a mass of plaque of degenerated, thickened arterial intima occurring in atherosclerosis. A thrombus is an aggregation of blood factors, primarily platelets and fibrin with entrapment of cellular elements, frequently causing vascular obstruction at the point of its formation. An embolus is a clot or other plug brought by the blood from another vessel and forced into a smaller one, thus obstructing the circulation, generally.

Many catheter-mounted devices are presently available for removing material from vessels. Some of these devices include rotatable abrasive members on the distal tip of a flexible catheter, which tend to remove hardened atherosclerotic materials without damaging the normal elastic soft tissue of the vessel wall. However, long standing needs remain.

Another material removal device is seen in the U.S. Pat. No. 5,423,799 to Shiu, and includes a tubular housing mounted on the distal end of a catheter within which a helical screw member rotates. The screw includes a sharp edge which, in cooperation with housing, cuts the tissue and draws it into the housing for later removal. Artisan recognize maceration issues with the devices and methods practiced under this patent.

Despite advances made in catheter-mounted material removal devices, many of them remain limited in their operational capacity, and tend to clog up fairly quickly. This necessitates the surgeon advancing very slowly through the material blockage, and greatly increases the length of surgery. In the worst-case, the device becomes irreversibly clogged, and must be removed and another device procured and substituted. Therefore, there remains a need for a more efficient catheter-mounted material removal device that can rapidly cut through a mass of blocking material without clogging. Likewise, an interventionist—friendly method and apparatus method remain outstanding.

BRIEF SUMMARY OF THE INVENTION

In one embodiment, the present invention provides a device for removing material from a body lumen including an elongate, flexible tube having distal and proximal ends and a passageway there through. The device has a material removal tip on the distal end including an outer housing rotationally fixed with respect to the tube and a rotating member within the housing. The housing includes a lumen extending from a distal open mouth to the tube passageway. The rotating member includes distal and proximal ends, a central body, and a plurality of circumferentially spaced flanges extending radially outward from the body. At least one shearing member is formed within the lumen of the housing and axially adjacent to the flange to cooperate with the flange and shear material received in the housing mouth. The shearing member may be located distally or proximal with respect to the flanges, or shearing members on both sides of the flanges may be provided. The housing desirably includes proximal and distal sections, each including lumens, and an annular groove larger than either the distal or proximal sections and formed therebetween for axially restraining the flanges on the rotating member. The shearing member is preferably located adjacent to the groove. The housing may be formed in one piece or two separate pieces.

In a preferred embodiment, the rotating member has a central body and a helical screw thread thereon and is driven by a drive shaft that extends through a catheter attached to the housing. The shearing member has a radial dimension that brings it into close proximity with an associated rotating member. That is, a distal shearing member is sized to come into close proximity with the central body of the rotating member, while a proximal shearing member is sized to come into close proximity with a drive shaft.

In another aspect, the present invention provides a material removal tip for use in a catheter-mounted material removal device, comprising a rotatable member having an outwardly projecting shearing member, and a generally tubular housing sized to receive the rotatable member. The housing includes a stationary shearing member located axially adjacent to the rotating shearing member. The stationary and rotating shearing members cooperate to chop material received within the housing, reducing the clogging propensity of the material. There is preferably a plurality of rotating shearing members axially restrained within a groove formed on the inner surface of the housing. The stationary shearing member is desirably located adjacent to groove, either proximally, distally, or both in the case of two stationary shearing members.

The present invention further provides a method of material removal, including advancing through a body lumen a catheter-mounted material removal device having distal material removal tip including a hollow housing and a rotatable member therewithin. The rotatable member is rotated to engage the material, which is then sheared in the housing between relatively rotating shearing members to reduce the clogging propensity of material. Subsequently, the sheared material is removed from within the housing as the device is further advanced through the body lumen.

BRIEF DESCRIPTION OF THE DRAWINGS

FIG. 2a is a longitudinal sectional view through one embodiment of a material removal tip of the present invention having a two-piece housing;

FIG. 2b is an end elevational view of the material removal tip having a two-piece housing, taken along line 2b—2b of FIG. 2a;

FIG. 2c is a sectional view of a stationary shearing member of the proximal housing section in operation, taken along line 2c—2c of FIG. 2b;

FIG. 2d is a sectional view of a stationary shearing member of the distal housing section in operation, taken along line 2d—2d of FIG. 2b;

FIG. 3a is a longitudinal sectional view through a proximal housing section of the material removal tip of FIG. 2a;

FIG. 3b is an end elevational view of the proximal housing section, taken along line 3b—3b of FIG. 3a;

FIG. 4a is a longitudinal sectional view through a distal housing section of the material removal tip of FIG. 2a;

FIG. 4b is an end elevational view of the distal housing section, taken along line 4b—4b of FIG. 4a;

FIG. 5b is an end elevational view of the material removal tip having a one-piece housing, taken along line 5b—5b of FIG. 5a;

FIG. 6a is a longitudinal sectional view through the one-piece housing of the material removal tip of FIG. 5a;

FIG. 6b is an end elevational view of the one-piece housing, taken along line 6b—6b of FIG. 6a;

FIG. 7a is a longitudinal sectional view through an alternative one-piece housing in accordance with the present invention;

FIG. 7b is an end elevational view of the alternative one-piece housing, taken along line 7b—7b of FIG. 7a;

DETAILED DESCRIPTION

The present inventors have discovered an improved method for percutaneous material to be made into small pieces and withdrawn from affected luminal spaces. Likewise, the instant teachings are physician/interventionist—friendly and useful.

Figure 1:
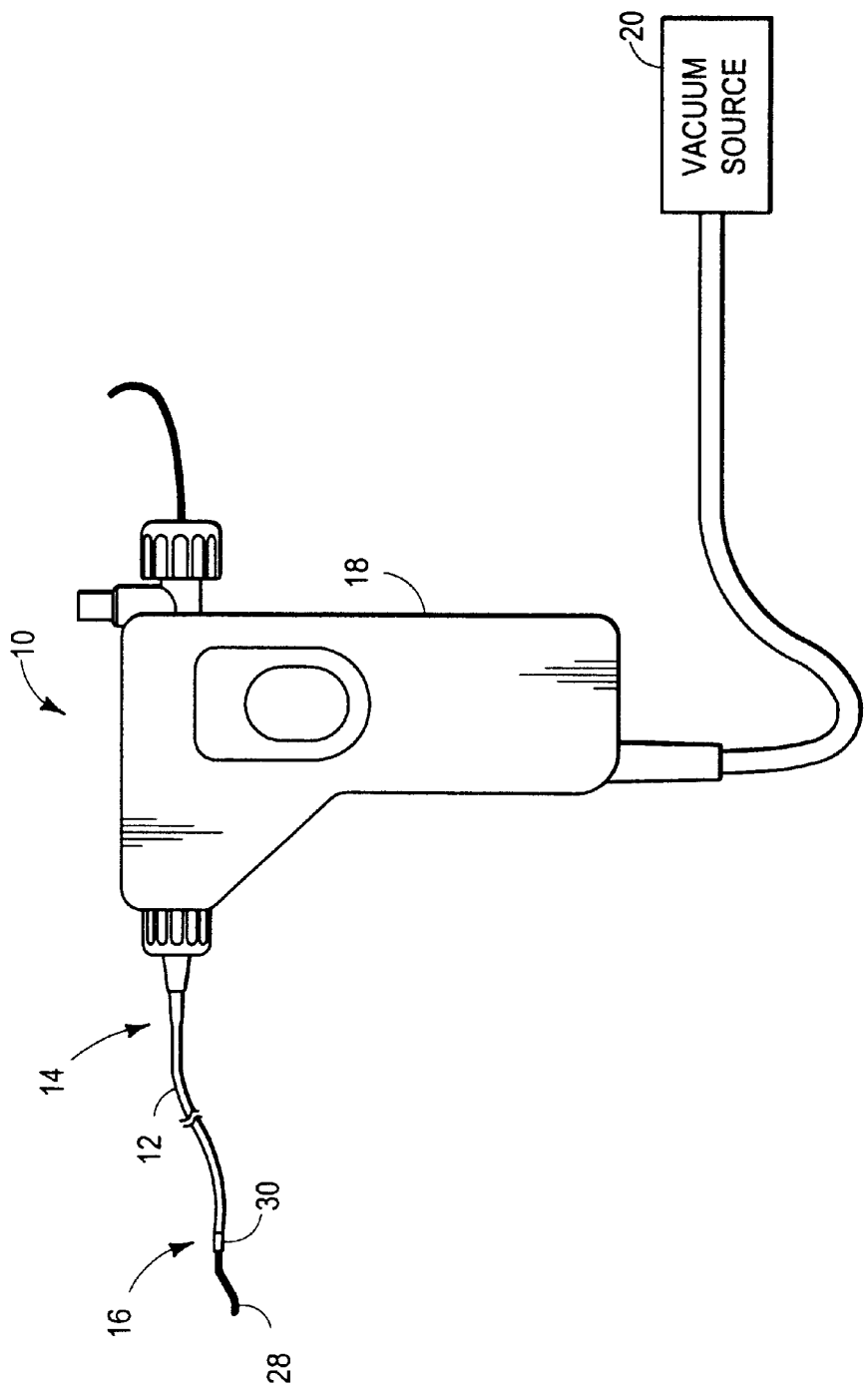
FIG. 1 is a schematic view of a hand-held material removal system within which the material removal device of the present invention is incorporated.

With reference to FIG. 1, a material removal system 10 suitable for use with the present invention comprises an elongate flexible tube 12 having a proximal end 14 and a distal end 16. A hand-held control 18 attached to the proximal end 14 of the tube 12 permits manipulation of the system. The control 18 carries electronic circuitry, controls, and indicators. A source of vacuum 20 communicates with the hand-held control 18 which in turn includes passages for creating a negative pressure in the interior of the tube 12. In addition, a drive motor (not shown) is mounted within the hand-held control 18 for supplying rotational motion to a flexible drive shaft 22 (FIG. 2a) extending through the elongated tube 12. A tubular removal passageway 24 is thus defined in the space outside of the drive shaft 22 and within the flexible tube 12. The drive shaft 22 is preferably hollow to permit passage therethrough of a guidewire 28.

The present invention provides an improved distal material removal tip 30, which is shown in detail in FIGS. 2, 3 and 4. The removal tip 30 comprises an outer housing 32 and a member 34 received therewithin for rotation about an axis 37. The outer housing 32 has a substantially hollow tubular shape and comprises a distal section 36 and a proximal section 38, through which a continuous lumen 40 extends. The lumen 40 is defined by a distal lumen 42 within the distal section 36; a proximal lumen 44 within the proximal section 38, and an annular groove 46 located intermediate the distal and proximal sections, all being axially aligned. In the illustrated embodiment, the groove 46 has a larger diameter than the distal lumen 42, which in turn has a larger diameter than the proximal lumen 44. The rotatable member 34 is received within the distal housing section 36, with a portion within the groove 46, as will be described below.

The aforementioned flexible tube 12 is seen in phantom coaxially received over a tubular body 50 on the proximal housing section 38. Likewise, the drive shaft 22 is seen in phantom extending through the flexible tube 12 and through the proximal lumen 44 into engagement with the rotatable member 34. In this manner, the drive shaft 22 and member 34 rotate together within the housing 32. A number of different drive shaft configurations may be utilized with the present invention, none of which should be construed as limiting. Both the elongated tube 12 and drive shaft 22 are seen in phantom in FIG. 2a, and thus are not seen in the end view of FIG. 2b.

As mentioned, the rotatable member 34 is partly received within the groove 46. More particular, the rotatable member 34 comprises a generally cylindrical or tubular body 56 from which a continuous helical screw thread 58 radially outwardly extends. The screw thread 58 begins at a distal face 60 of the member 34 and continues around the body 56 for approximately two-thirds of its length. A plurality of cantilevered fingers 62 defined by longitudinal slots 64 are provided on the proximal end of the member 34. Each of the fingers 62 carries an outwardly extending cutter or flange 66, each of which in axial projection has a generally truncated triangular shape as seen in FIG. 2b. There are preferably three such flanges 66 evenly circumferentially spaced and forming somewhat of a propeller configuration about the rotatable member 34. The flanges 66 terminate in outer tips that together define a circle having a diameter greater than the diameter of the distal lumen 42, but less than the diameter of the groove 46.

Figure 3A:
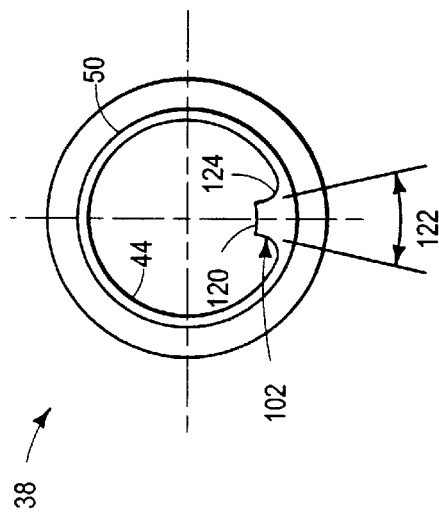
Figure 3B:
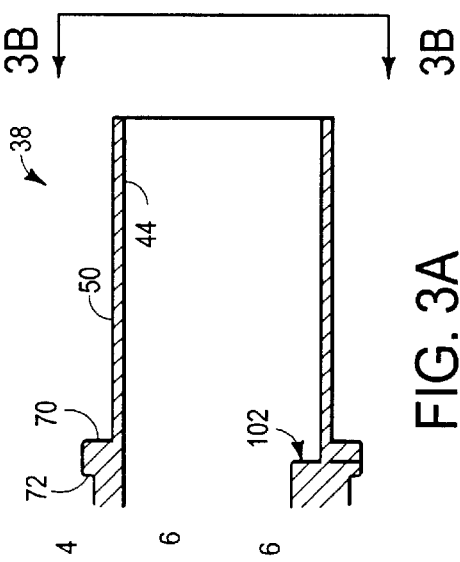

With reference to FIGS. 3a and 3b, the proximal housing section 38 includes the tubular body 50 terminating on its distal end in a radially outwardly extending annular shoulder 70 having a diameter that is reduced at a step 72 to a cylindrical land 74 ending at a distal face 76.

Figure 4A:
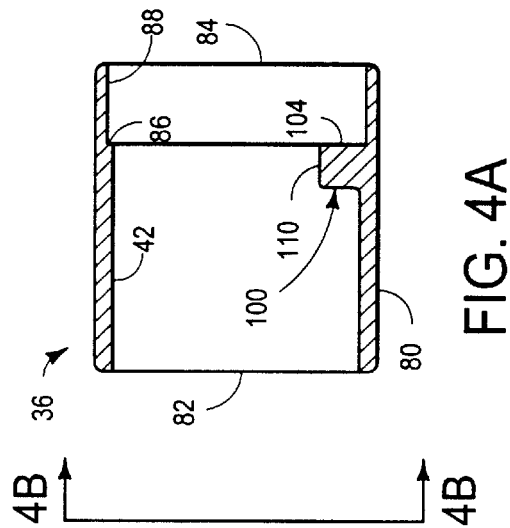
Figure 4B:
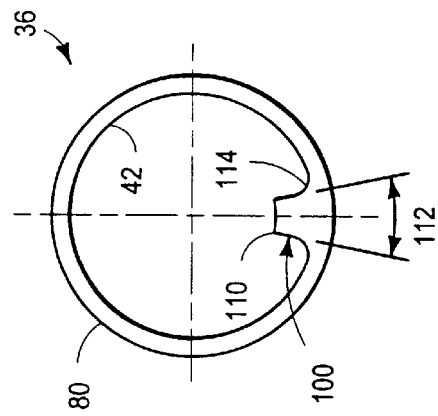

And seen in FIGS. 4a and 4b, the distal housing section 36 also includes a tubular body 80 extending from a distal mouth 82 to a proximal end 84. The lumen 42 extends proximally from the mouth 82 until a step 86 increases the diameter to that of a stepped bore 88.

The land 74 of the proximal housing section 38 has a diameter that is approximately equal to the diameter of the bore 88. Consequently, the distal end of the proximal housing section 38 is closely received within the bore 88 until the proximal end 84 contacts the step 72. By cooperation between the distal and proximal sections 36, 38, the groove 46 is defined on its outer side by the bore 88, and on respective axial sides by the distal face 76 of the proximal housing section 38 and the step 86 of the distal housing section 36. The rotatable member 34 is captured in the location of FIG. 2a by cooperation between the outwardly projecting flanges 66 and the groove 46. The cantilevered fingers 62 enable inward deflection of the flanges 66 so that they can pass through the distal lumen 42 of the housing 32 and snap outward into the groove 46. The spacing between the flanges 66 and the groove 46 are slightly exaggerated in the drawings, and in a working model of the device the axial dimension of the flanges 66 will be slightly smaller than the spacing between the step 86 and the distal face 76. In this manner, the flanges 66 are constrained in the groove 46 from even slight axial movement.

The present invention provides at least one shearing member that is axially adjacent the flanges 66. In the embodiment of FIGS. 2–4, there are two such shearing members, a distal member 100 and a proximal member 102. The distal shearing member 100 projects radially inwardly with respect to the distal lumen 42 of the distal housing section 36. Likewise, proximal shearing member 102 projects radially inwardly with respect to the proximal lumen 44 of the proximal housing section 38. As seen best in FIG. 4a, the distal shearing member 100 has a proximal face 104 which is co-extensive with the step 86. The proximal face 104 is thus positioned on the edge of the groove 46 closely adjacent to the rotating flanges 66. In like manner, as seen in FIG. 3a, the proximal shearing member 102 has a distal face 106 which is co-extensive with the distal face 76 of the proximal housing section 38. The distal face 106 is thus positioned on the edge of the groove 46 closely adjacent to the rotating flanges 66.

With reference to the detailed views of FIGS. 3–4, the shearing members 100, 102 in a preferred embodiment resemble teeth. More specifically, the distal shearing member 100 includes an arcuate inner face 110 having a relatively small included angle 112 and transition surfaces 114 on either side joining the inner face to the distal lumen 42. The proximal shearing member 102 includes an arcuate inner face 120 having an included angle 122 and transition surfaces 124 on either side joining the inner face to the proximal lumen 44. The small included angles 112, 122 and generally radially oriented transition surfaces 114, 124 define shearing members 100, 102 of relatively small angular size. The angular size must of course be sufficient to provide shearing strength in operation, as will be described, but should be kept to a minimum to reduce the obstruction to flow of material through the housing 32.

As seen in FIG. 2a, each of the shearing members 100, 102 has a radial dimension sufficient to bring its respective inner face 110, 120 into close proximity with an adjacent rotating element. That is, the inner face 110 of the distal shearing member 100 is spaced across a gap 130 from the body 56 of the rotatable member 34. Similarly, the inner face 120 of the proximal shearing member 102 is spaced across a gap 132 from the drive shaft 22. The gaps 130 and 132 are preferably minimized without risking contact between the respective rotating element and shearing member. Illustrative numerical ranges are presented herewith, and will be known by artisans to be exemplary and not limiting. More specifically, the gaps 130 and 132 are each desirably greater than zero but less than 0.254 mm (0.01 inches). More preferably, the gaps 130 and 132 are each less than 0.0254 mm (0.001 inches), and most preferably the gaps are each less than 0.0127 mm (0.0005 inches).

Each of the inner faces 110, 120 of the shearing members 100, 102 preferably has an arcuate surface concentric with the axis of rotation of the adjacent rotating element. In addition, the inner faces 110, 120 preferably have a radius of curvature that corresponds to the adjacent rotating elements. Namely, the distal shearing member 100 has an inner face 110 that is the same radius of curvature as the body 56 of the rotatable member 34, and the inner face 120 of the proximal shearing member 102 has a curvature that is the same as the external diameter of the drive shaft 22. In one embodiment, merely offered for consideration as an illustration of the teachings of the present invention, the radius of curvature of the inner face 110 is about 1.194 mm (0.047 inches), and the radius of curvature of the inner face 120 is about 0.991 mm (0.039 inches).

As illustrated in FIG. 2b, the distal shearing member 100 is oriented 180 degrees about the housing 32 with respect to the proximal shearing member 102. In practice, the relative orientation of the shearing members 100, 102 about the housing 32 is not considered especially significant. Therefore, the shearing members 100, 102 may be axially aligned, or offset with respect to one another around the circumference of the housing 32 at any relative orientation.

The axial and circumferential dimensions of each of the shearing members 100, 102 must be sufficient to provide adequate strength without inordinately blocking the lumen 40 through the housing 32. In one embodiment, for example, it has been discovered that the distal lumen 42 has a diameter of approximately 1.75 mm (0.069 inches), and the distal shearing member 100 has an axial dimension of approximately 0.279 mm (0.011 inches) and an included angle of approximately 25 degrees. In the same embodiment, the proximal lumen 44 has a diameter of approximately 1.42 mm (0.056 inches), and the proximal shearing member 102 has an axial dimension of approximately 0.318 mm (0.0125 inches) and an included angle about of 25 degrees. Relative measurements and dimensional sizing, are included merely to demonstrate utility of the instant teachings, and are not intended to limit them.

In use, the material removal tip 30 is inserted into a body vessel or other cavity using the aforementioned guidewire 28 and conventional catheter introduction techniques not described further herein. The distal tip 30 is manipulated into close proximity with the target blockage or material deposit, the drive shaft 22 rotated, and the vacuum source 20 actuated. As the distal tip 30 is advanced toward the material to be removed, the suction created at the mouth 82 tends to pull material into contact with the rotatable member 34 and screw thread 58. The combination of suction and "Archimedes Screw" action of the screw thread 58 draws material into the distal housing section 36, and ultimately into contact with the rotating flanges 66. As the material is drawn through the distal housing section 36, the screw thread 58 performs a coarse chopping, reducing the largest material agglomerations in size. Subsequently, the rotating flanges 66 more finely chop the material to reduce clogging of the tubular passageway between the drive shaft 22 and first the proximal lumen 44 and then the inner surface of the elongated tube 12.

It has been found that without a shearing member, such as provided by the distal and proximal members 100, 102, material tends to build up on the axially-facing surfaces of the flanges 66. Eventually, buildup of material occludes the circumferential spaces between the flanges 66, greatly diminishing the capacity of material removal, and in some instances irreversibly clogging the device. Consequently, the present invention provides one or more shearing members to cut or otherwise knock material from the axially facing surfaces of the rotating flanges 66. Because of the relative movement between the flanges 66 and shearing members 100, 102, the discontinuous circumferential projection of the shearing members, and the close axial spacing between these relatively moving surfaces, material is effectively sheared from the axially facing surfaces of the flanges 66. Any material sheared from the flanges 66 is then exhausted in a proximal direction through the annular passageway 24 within the elongated tube 12. The flanges 66 are thus maintained clear of material, and their corners thus remain unobstructed and effective in finely chopping the material that reaches them.

With reference to FIGS. 3 and 4, the proximal face 104 of the distal shearing member 100 and the distal face 106 of the proximal shearing member 102 are preferably oriented normal to the axis of rotation 37 of the member 34. In addition, the transition surfaces 114, 124 are preferably axially oriented. As seen in FIGS. 2c and 2d, therefore, the cross-sections (taken circumferentially) of the shearing members 100, 102 are rectangular, and shearing edges 116, 126 are defined by perpendicular corners that face the leading edges of the oncoming flanges 66. The leading edges of each of the flanges 66 are likewise defined by perpendicular corners 68 so that the passage of the flanges 66 past the shearing members 100, 102 creates a scissor-like action, serving not only to clear material from the axial surfaces of the flanges 66 but also to sever fibrous matter present in any material caught therebetween. Alternatively, one or both of the cooperating edges on the flanges 66 and shearing members 100, 102 may be sharpened to knife edges to further facilitate the severing action, although there may be a limit to such sharpening dictated by strength considerations. FIG. 2c shows one flange 66 having material adhered thereto and approaching the proximal shearing member 102, while FIG. 2d shows another flange 66 having just passed the distal shearing member 100 and been cleared of material.

To further facilitate the two functions of the shearing members 100, 102 (i.e., clearing material from the axial surfaces of the flanges 66 and also severing fibrous matter), the transition surfaces 114, 124 each have a radial portion that gradually transitions to blend into the base lumen wall, as seen in FIGS. 3b and 4b. That is, the transition surface 114 gradually curves into tangency with the wall of the distal lumen 42, and the transition surface 124 gradually curves into tangency with the wall of the proximal lumen 44. The curvilinear transition surfaces 114, 124 thus provide a radial shear component between the respective shearing edges 116, 126 and leading edges 68 of the rotating flanges 66. It will be clear, therefore, that the shearing action is scissor-like (as opposed to unidirectional shear) as the oncoming leading edge 68 of each flange 66 first reaches the radially outermost portion of each shearing edge 116 or 126, and then gradually reaches the rest of the shearing edge. This is preferred over a situation where the flange leading edge 68 reaches the entire shearing edge at once, which would be the case if the surfaces 114, 124 were entirely radially disposed. Of course, the latter arrangement is not precluded while still obtaining most of the benefits of the present invention.

Figure 5B:
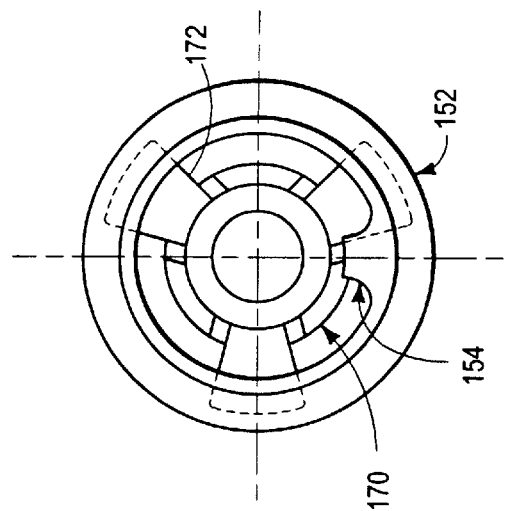
Figure 5A:
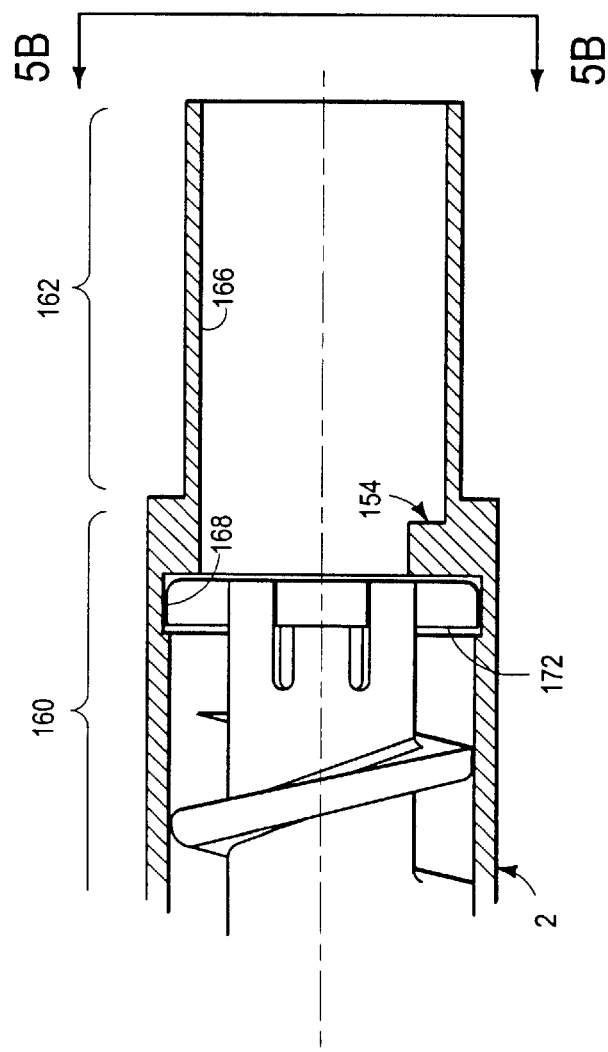
FIG. 5a is a longitudinal sectional view through a second embodiment of a material removal tip of the present invention having a one-piece housing.

As mentioned above, various other configurations of the material removal tip 30 are contemplated. For example, FIGS. 5–6 illustrate a material removal tip 150 having a one-piece housing 152 and a single shearing member 154. As before, the housing 152 includes a distal section 160, a proximal section 162, a distal lumen 164, a proximal lumen 166, and an intermediate groove 168. Likewise, the rotating member 170, identical to the member 34 previously described, includes outwardly projecting flanges 172 that are axially restrained within the groove 168. The elongated tube and drive shaft are not shown in FIG. 5a for clarity.

As seen best in FIGS. 6a and 6b, the shearing member 154 is located just proximal to the groove 168, and thus corresponds to the proximal shearing member 102 described for the first embodiment. There is no distal shearing member in this embodiment. It all other aspects, the shearing member 154 is identical to the proximal shearing member 102 described above, and includes an arcuate inner face 174 spanning an included angle 176, transition surfaces 178, and a distal face 180 coincident with the proximal boundary of the groove 168. The distal face 180 is thus axially adjacent the rotating flanges 172 and serves to knock material from the proximal faces of the flanges.

Although only one shearing member is shown located either distally or proximally with respect to the groove, those skilled in the art will recognize that two or more shearing members on either side can also be provided. It has been found that a single shearing member is sufficient to knock material from the axially facing surfaces of the flanges, and is preferred because it minimizes the obstruction to flow of material from the distal to the proximal sections of the housing. Likewise, as mentioned above, a shearing member provided of only one side of the rotating flanges is believed to significantly improve performance of the device. Thus, as seen in FIGS. 5–6, a single shearing member 154 is provided proximal to the rotating flanges 172, and another alternative not illustrated is a single shearing member located distally with respect to the flanges.

A still further embodiment of the present invention is seen in FIGS. 7a and 7b. In these views, an alternative one-piece housing 200 is shown for use with a rotating member, such as the members 34 or 170 described previously. Again, the housing 200 includes a distal section 202, a proximal section 204, a distal lumen 206, a proximal lumen 208, and an intermediate groove 210. A distal shearing member 220 and a proximal shearing member 222 are located on opposite sides and adjacent to the groove 210. The shearing members 220 and 222 are aligned circumferentially, as seen in the end view of FIG. 7b.

The choice of using a one- or two-piece housing depends upon the manufacturing choices available. A one-piece housing is preferred if tooling for forming the shearing members 220, 222 on the inner surface thereof is really available. On the other hand, forming the inner shearing members on the mating ends of each section of a two-piece housing is somewhat easier, and the two sections can then be joined and welded or otherwise fastened together.

A number of different materials are suitable for the material removal device, including stainless-steel, titanium, acrylic or other suitable biocompatible and rigid materials. The selection of material may be dictated by the particular manufacturing process used. In a preferred embodiment, the material removal device housing is formed in two sections of stainless-steel and includes a single shearing member on each side of the rotating flanges. The two sections are preferably laser welded together.

Figure 8A:
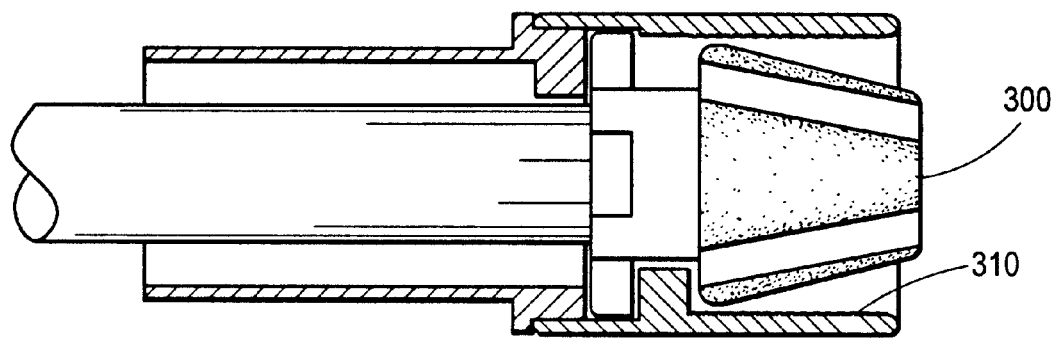
FIG. 8a is a longitudinal sectional view through yet a still further embodiment of a material removal tip of the present invention wherein the rotatable member includes a grinding means, according to the instant teachings, and, FIG. 8b is an end elevational view of still yet another grinding means of the present invention.
Figure 8B:
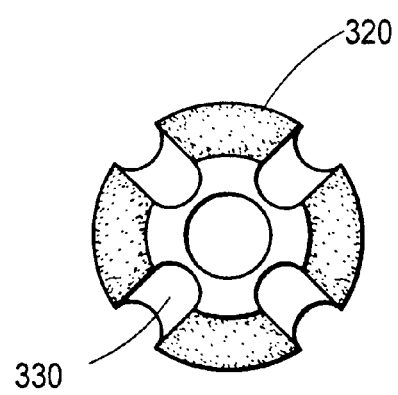

Another embodiment is shown in FIG. 8A and FIG. 8B, wherein the rotatable member of the invention includes a grinder rotor 300 for grinding material between abrasive surface 320 on the grinder rotor and abrasive surface 310 in the housing of the device. This embodiment may further include at least one cutting flute 330 to aid the grinding. In the embodiment shown in FIG. 8A and FIG. 8B, grinding of the material takes place prior to contact of the material with the shearing member. Abrasive surfaces 310 and 320 may be fabricated from one or more abrasive materials such as ceramics, diamond, quartz, silicon carbide, aluminum oxide, boron carbide, boron nitride, tungsten carbide and titanium nitride. Alternatively, abrasive surfaces 310 and 320 can be titanium or stainless steel surfaces with a ridged, file-like surface.

Stated briefly, the various embodiments of the invention include a method of removing material from a body lumen in a patient in need of such removal, comprising advancing a catheter-mounted device having a distal material removal tip including a hollow housing and a member rotatable therewithin, rotating the rotatable member, drawing the material into the housing, shearing the material in the housing between relatively rotating shearing members to reduce the clogging propensity of the material, removing the sheared material from within the housing as the material removal tip is advanced through the vessel.

The method may further include first coarsely chopping the material in the housing, and then finely chopping the material in the housing during the step of shearing.

In another embodiment of the invention, the method utilizes a rotatable member that includes a screw thread. Here, the step of coarsely chopping the material in the housing is accomplished by contact between the screw thread and the material. In another embodiment of the method, the step of shearing includes cutting material in a scissor-like manner between opposed shearing edges provided on the relatively rotating shearing members. Here, the opposed shearing edges define shearing planes for simultaneous coarse, medium and fine shearing, wherein the shearing planes comprise a range of dimensions up to about 0.05 mm (about 0.002 inches).

The method may involve a catheter-mounted device having a distal material removal tip that has a total preselected diameter effective for use in a preselected body lumen, which may be a blood vessel, a lumen for the passage of bile, a lumen for the passage of urine, a lymph vessel, a gastrointestinal lumen, and the like.

Still another embodiment involves a method of removing material from and treating a body lumen with a medically useful agent in a patient in need of such removal and treatment, comprising advancing a catheter-mounted device having a distal material removal tip including a hollow housing and a member rotatable therewithin, the device further comprising a lumen, wherein the lumen is adapted to contain a medically useful agent for release at a predetermined time; rotating the rotatable member, drawing material into the housing, shearing the material in the housing between relatively rotating shearing members to reduce the clogging propensity of the material, removing the sheared material from within the housing as the material removal tip is advanced through the vessel; and, releasing the medically useful agent at the predetermined time. The release may be accomplished by pumping means, such as gas pressure, mechanical pressure, liquid pressure, and the like. The medically useful agent may be an x-ray contrast agent, a thrombolytic agent, a viral vector, an enzyme such as a proteolytic enzyme, and the like.

In another embodiment of the method, portions of the shearing members are coated or fabricated using ceramics, diamond, quartz, silicon carbide, aluminum oxide, boron carbide, boron nitride, tungsten carbide, titanium nitride and the like, whereas the rotatable member and tubular housing are constructed using stainless steel, titanium, acrylic plastic and the like biocompatible materials.

In another embodiment, the invention teaches a method of removing material from a body lumen in a patient in need of such removal, comprising advancing a catheter-mounted device having a distal material removal tip including a hollow housing and a member rotatable therewithin, wherein the rotatable member includes grinding means for grinding the material, rotating the rotatable member, grinding the material into ground material, drawing the ground material into the housing, shearing the material in the housing between relatively rotating shearing members to reduce the clogging propensity of the material, removing the sheared material from within the housing as the material removal tip is advanced through the vessel. The grinding means may be fabricated from such abrasive materials as ceramics, diamond, quartz, silicon carbide, aluminum oxide, boron carbide, boron nitride, tungsten carbide, titanium nitride, and the like, including interactive media.

In another embodiment, the invention provides an article of manufacture, comprising packaging material and instructional material for the use of the method. The article of manufacture may further include percutaneous material removal devices, guidewires, introducers, containers, catheters, angioplasty balloons, stents, medicinal agents, medical syringes, and the like. The instructional material may include printed materials, GD disks, magnetic data storage disks, videotapes, and the like.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope, as if the same were literally set forth herein.

What is claimed is:

1. A method of removing material from a body lumen in a patient, the method comprising:

advancing through said body lumen a catheter-mounted device having a distal material removal tip comprising a hollow housing, a member rotatable therewithin, and a shearing member;

rotating the rotatable member;

drawing said material into said housing;

shearing said material in said housing between said rotating rotatable member and the shearing member, whereby the propensity of said material to clog said device is reduced; and removing said material from within said housing as said material removal tip is advanced through said body lumen.

2. The method of claim 1, further including:

first coarsely chopping said material in said housing; and then, finely chopping said material in said housing during said step of shearing.

3. The method of claim 2, wherein said rotatable member includes a screw thread and said step of coarsely chopping said material in said housing is accomplished by contact between said screw thread and said material.

4. The method of claim 1, wherein the shearing member comprises opposed shearing edges and the step of shearing the material includes cutting the material in a scissor-like manner between the opposed shearing edges.

5. The method of claim 4, wherein said opposed shearing edges define shearing planes for simultaneous coarse, medium and fine cutting.

6. The method of claim 5, wherein said opposed shearing edges define said shearing planes comprising a range of dimensions up to about 0.05 mm (about 0.002 inches) for simultaneous coarse, medium and fine shearing.

7. The method of claim 1 wherein said catheter-mounted device having a distal material removal tip has a total preselected diameter effective for use in said preselected body lumen.

8. The method of claim 7 wherein said preselected body lumen is selected from the group consisting of blood vessels, lymph vessels, lumens for the passage of bile, lumens for the passage of urine, and gastrointestinal lumens.

9. The method of claim 1 wherein said catheter-mounted device further comprises a device lumen adapted to release a medically useful agent, the method further comprising:

releasing said medically useful agent into said body lumen from said device lumen.

10. The method of claim 9, wherein said release is accomplished by pumping means.

11. The method of claim 10, wherein said pumping means is selected from the group consisting of gas pressure, mechanical pressure, and liquid pressure.

12. The method of claim 9, wherein said medically useful agent is an x-ray contrast agent.

13. The method of claim 9, wherein said medically useful agent is a thrombolytic agent.

14. The method of claim 9, wherein said medically useful agent is a viral vector agent.

15. The method of claim 9, wherein said medically useful agent is an enzyme.

16. The method of claim 9, wherein said enzyme is a proteolytic enzyme.

17. The method of claim 1, wherein portions of said shearing member are coated with at least one material selected from the group consisting of ceramics, diamond, quartz, silicon carbide, aluminum oxide, boron carbide, boron nitride, tungsten carbide and titanium nitride.

18. The method of claim 1, wherein portions of said shearing members are fabricated from at least one material selected from the group consisting of ceramics, diamond, quartz, silicon carbide, aluminum oxide, boron carbide, boron nitride, tungsten carbide and titanium nitride.

19. The method of claim 1, wherein said rotatable member and said generally tubular housing are constructed substantially of at least one material selected from the group consisting of stainless steel, titanium, and acrylic plastic.

20. An article of manufacture, comprising packaging material and instructional material for the use of the method of claim 1.

21. The article of manufacture of claim 20, further including at least one item selected from the group consisting of percutaneous material removal devices, guidewires, introducers, containers, catheters, angioplasty balloons, stents, medicinal agents, and medical syringes.

22. The article of manufacture of claim 20, wherein said instructional material is at least one device selected from the group consisting of printed materials, CD disks, magnetic data storage disks, and videotapes.

23. A method of removing material from a preselected body lumen in a patient in need of such removal, comprising:

advancing through said preselected body lumen a catheter-mounted device having a distal material removal tip including a hollow housing, a shearing member and a member rotatable therewithin, wherein said rotatable member includes grinding means for grinding said material prior to said contact of said material with said shearing member, wherein said grinding means include at least one abrasive surface fabricated from at least one abrasive material selected from the group consisting of ceramics, diamond, quartz, silicon carbide, aluminum oxide, boron carbide, boron nitride, tungsten carbide, titanium nitride, titanium surfaces with a file-like surface, and stainless steel surfaces with a file-like surface;

rotating said rotatable member;

grinding said material into ground material;

drawing said ground material into said housing;

shearing said material in said housing between the rotating rotatable member and shearing member, whereby the propensity of said material to clog said device is reduced; and removing said material from within said housing as said material removal tip is advanced through said preselected body lumen.

24. The method of claim 23, wherein said rotatable member includes a grinder rotor having at least a first abrasive surface, and said housing includes at least a second abrasive surface.

* * * * *